United States Patent [19]

Cuif et al.

[11] Patent Number: 6,037,305
[45] Date of Patent: Mar. 14, 2000

[54] USE OF CE/ZR MIXED OXIDE PHASE FOR THE MANUFACTURE OF STYRENE BY DEHYDROGENATION OF ETHYLBENZENE

[75] Inventors: Jean-Pierre Cuif, Princeton, N.J.; Anne-Marie Le Govic, Paris, France

[73] Assignees: Rhodia Chimie, Courbevoie, Cedex, France; Rhodia Inc., Cranbury, N.J.

[21] Appl. No.: 08/810,559

[22] Filed: Mar. 3, 1997

[51] Int. Cl.⁷ ............................ B01J 21/06; B01J 23/10; B01J 23/04
[52] U.S. Cl. .......................... 502/304; 502/300; 502/302
[58] Field of Search ................................. 502/300, 302, 502/304

[56] References Cited

U.S. PATENT DOCUMENTS

| | | | |
|---|---|---|---|
| 3,733,327 | 5/1973 | Vrieland et al. | |
| 4,758,543 | 7/1988 | Sherrod et al. | 502/174 |
| 5,023,225 | 6/1991 | Williams et al. | 502/304 |
| 5,171,914 | 12/1992 | Hamilton, Jr. | 585/444 |
| 5,532,198 | 7/1996 | Chopin et al. | 502/304 |
| 5,571,492 | 11/1996 | Yao et al. | 502/304 |
| 5,607,892 | 3/1997 | Chopin et al. | 502/304 |

FOREIGN PATENT DOCUMENTS

| | | | |
|---|---|---|---|
| 3506022 A1 | 8/1986 | Germany | B01J 23/76 |
| 3521766 A1 | 1/1987 | Germany | B01J 23/74 |

OTHER PUBLICATIONS

Derwent Abstract 97–010,339 of SU 1,515,471, Apr. 1996.
* English language abstracts of DE 3521766 (Jan. 1987) and DE 3506022 (Aug. 1986) are provided and are attached to the German language patent references. *Considered to the Extent of Abstracts.

*Primary Examiner*—Elizabeth D. Wood
*Attorney, Agent, or Firm*—Katherine L. Carleton

[57] ABSTRACT

The present invention relates to an improved active support, cerium/zirconium mixed oxides or cerium/zirconium solid solutions, for improved dehydrogenation catalysts useful in converting alkylaromatics to alkenylaromatics, e.g., ethylbenzene to styrene.

12 Claims, No Drawings

USE OF CE/ZR MIXED OXIDE PHASE FOR THE MANUFACTURE OF STYRENE BY DEHYDROGENATION OF ETHYLBENZENE

TECHNICAL FIELD

The present invention relates to an improved active support, cerium/zirconium mixed oxides or cerium/zirconium solid solutions, for improved dehydrogenation catalysts useful in converting alkylaromatics to alkenylaromatics, e.g., ethylbenzene to styrene.

BACKGROUND OF THE INVENTION

The most common catalysts used in industry to manufacture styrene by dehydrogenation of ethylbenzene are based on iron (Fe), potassium (K) and cerium (Ce). The preparation of these catalysts consists of reacting a basic potassium salt, such as potassium carbonate, with an organic iron salt, EDTA for example. A possible active phase for the catalysis of dehydrogenation of ethylbenzene may be $K_2FeO_5$. It has been discovered that cerium oxide has an effect on the improvement of the yield and the selectivity of the Fe/K based catalytic system. In the so called bulk catalyst, the amount of cerium is generally about 5 to about 10 weight percent. See U.S. Pat. No. 5,171,914, Shell Oil Co., issued Aug. 30, 1991; U.S. Pat. No. 5,023,225, United Catalysts Inc., issued Jul. 21, 1989; and German Patent DE 3,506,022, BASF A.G., issued Feb. 21, 1985.

The source of cerium used to make the catalyst can be cerium carbonate which is mixed together with the slurry of iron and potassium salts. Then, the slurry is calcined at high temperature, up to about 800° C. This temperature is required to prepare the active iron/potassium phase and to obtain cerium oxide ($CeO_2$). Like any catalyst, high surface area and thermal stability are needed in order to obtain higher activity. However, calcination of salts does not lead necessarily to high surface area materials.

In addition, it was discovered more recently that a higher cerium content compared to bulk catalysts can improve the selectivity and yield of the reaction. See German Patent DE 3,521,766, BASF A.G., issued Jun. 19, 1985 and U.S. Pat. No. 4,758,543, Dow Chem. Co., issued Jul. 19, 1988. As a conclusion of these studies, cerium oxide could be used as support for the Fe/K active phase. io However, the standard cerium oxide material has shown a very poor thermal stability at high temperature, particularly at temperatures higher than 800° C.

Some additional compounds based on cerium have also been utilized. For example, cerium phosphate and Ce—Zr phosphates were found to be good catalysts for oxydehydrogenation of alkylaromatics and alkylpyridines. See U.S. Pat. No. 3,733,327, Dow Chemical Co., issued Jun. 28, 1971.

Moreover, the oxygen storage capacity (OSC) of ceria has been suspected to be responsible for the activity of cerium oxide. Thus, higher OSC materials can be taken into account for styrene catalysis. One of the effects of ceria is the decocking of the catalyst that may be poisoned after a period of time under reducing conditions.

The object of the present invention is to use stabilized Ce/Zr mixed oxide phases or solid solutions as active supports of a Fe/K based catalyst for the manufacture of styrene by dehydrogenation of ethylbenzene. The (Ce,Zr)$O_2$ mixed oxides and preferably solid solutions present a very high thermal stability at high temperature as opposed to pure $CeO_2$. They also show an improved OSC compared to ceria. These materials can be obtained by co-precipitation and co-thermohydrolysis.

SUMMARY OF THE INVENTION

The present invention relates to an improved active support, cerium/zirconium mixed oxides or cerium/zirconium solid solutions, for improved dehydrogenation catalysts useful in converting alkylaromatics to alkenylaromatics, e.g., ethylbenzene to styrene.

Unless otherwise stated, all parts, ratios or percentages are by weight.

"Comprising" as used herein, means various components can be conjointly employed. Accordingly, the terms, "consisting essentially of" and "consisting of" are embodied in the term "comprising."

DETAILED DESCRIPTION OF THE INVENTION

The thermal stability of inorganic compounds can be defined as the stability of the surface area when the material is aged at high temperature. For many applications, particularly catalysis, high surface area and highly stable materials are required by end users. In accordance with the present invention, cerium and zirconium mixed oxides and solid solutions are produced having good thermal stability.

The present invention relates to an improved active support, cerium/zirconium mixed oxides or cerium/zirconium solid solutions, for improved dehydrogenation catalysts useful in converting alkylaromatics to alkenylaromatics, preferably ethylbenzene to styrene. The stabilized Ce/Zr mixed oxide phases or solid solutions are preferably utilized as active supports of a Fe/K based catalyst for the manufacture of styrene by dehydrogenation of ethylbenzene. The (Ce,Zr)O2 mixed oxides and preferably solid solutions present a very high thermal stability at high temperature as opposed to pure $CeO_2$. They also demonstrate an improved OSC compared to ceria. These materials can be obtained by co-precipitation and co-thermohydrolysis.

The (Ce,Zr)$O_2$ mixed oxides and solid solutions are formed by conventional processes such as co-thermohydrolysis or co-precipitation. Each of these processes is generally described separately below.

Co-thermohydrolysis

The first stage of the co-thermohydrolysis process involves preparing a mixture, in aqueous medium, of at least a soluble cerium compound, preferably a salt, and at least a soluble zirconium compound, preferably a salt. The mixture can be obtained either from solid compounds which are dissolved in water, or directly from aqueous solutions of these compounds, followed by mixing, in any order, of the defined solutions.

Of the water soluble cerium compounds, one example is Ce IV salts, such as nitrates including ceric ammonium nitrate, that are suitable for the present invention. Preferably, a cerium nitrate is used. The Ce IV salt solution can contain some Ce ll. However, it is preferred that the salt contains at least about 85% Ce IV. An aqueous solution of cerium nitrate can be used which is obtained by the action of nitric acid on a hydrated ceric oxide, prepared by a standard reaction of Ce III salt solution, carbonate for instance prepared in a conventional manner, for example by the action of nitric acid on the cerous carbonate and addition of an ammonia solution in the presence of an oxidizing agent, preferably hydrogen peroxide. Ceric nitrate solutions obtained by electrolytic oxidation of a cerous nitrate may also be used.

The aqueous solution of Ce IV salt can have some free acid, for instance a normality ranging from about 0.1 to about 4 N. In the present invention, it is possible to use either a solution containing some free acid or a pre-neutralized solution by addition of a base, such as an aqueous solution of ammonia or alkaline hydroxides, e.g., sodium, potassium, etc. Preferably an ammonia solution is used to reduce the free acidity. In this case, it is possible to define the neutralization rate (r) of the initial solution by the following equation:

$$r=(n_3-n_2)/n_1$$

wherein $n_1$ represents the total number of moles of Ce IV present in the solution after neutralization, $n_2$ represents the number of $OH^-$ ions effectively used to neutralize the initial free acidity from the Ce IV aqueous solution, and $n_3$ represents the total number of moles of $OH^-$ ions from the base added. When a neutralization step is used, excess base can be used in order to ensure the complete precipitation of the $Ce(OH)_4$ species. Preferably, r is lower than about 1, more preferably about 0.5.

The soluble zirconium salts used in the invention can be, for instance, zirconium sulfate, zirconyl nitrate or zirconyl chloride.

The amount of cerium and zirconium contained in the mixture substantially corresponds to the stoichiometric proportion required to obtain the final desired composition.

Once the mixture is obtained, it is then heated. This thermal treatment, called thermohydrolysis, is carried out at a preferred temperature of between about 80° C. and the critical temperature of the reacting medium, typically between about 80 and about 350° C., more preferably between about 90 and about 200° C.

The heating stage can be carried out under air or under an inert gas such as nitrogen. Any suitable reaction time can be used, usually between about 2 and about 24 hours. The thermal treatment can be performed under atmospheric pressure or under any higher pressure such as the saturated vapor pressure. When the temperature is higher than the reflux temperature of the reaction medium (usually higher than about 100° C.), for instance between about 150 and about 350° C., the reaction is performed in a closed reactor or autoclave. The pressure can be equal to the autogenic pressure and can be correlated to the chosen temperature. It is also possible to increase the pressure in the reactor. If required, some additional base can be added directly after the heating stage into the reaction medium in order to improve the yield of the reaction.

After the heating stage, a solid precipitate is recovered from the reactor and separated from the mother liquor by any known process for example filtration, settling or centrifugation.

The obtained precipitate can be washed or, in another embodiment, the precipitate is then dried, under air conditions for instance, at a temperature ranging from about 80 to about 300° C., preferably from about 100 to about 150° C. The drying stage is preferably performed until substantially no more weight loss is observed.

After the optional drying step, the recovered precipitate is then calcined. This allows the formation of a crystalline phase. Usually, the calcination is carried out at temperatures ranging from about 200 to about 1000° C. The calcination temperature is typically higher than about 300° C., and preferably ranges from about 400 to about 800° C.

Co-precipitation

The first stage of the co-precipitation process is the preparation of a mixture in an aqueous medium of at least a soluble cerium compound, preferably a salt, and at least a soluble zirconium compound, preferably a salt, or both. The mixture can be obtained either from solid compounds which are dissolved in water, or directly from aqueous solutions of these compounds, followed by mixing, in any order, of the defined solutions.

The cerium salt solution used can be any aqueous cerium salt solution, in the cerous and or ceric state, which is soluble in the conditions of preparation, in particular a cerous chloride or cerium nitrate solution in the cerous or ceric state or a mixture of the same. The zirconium salt solution used can be any aqueous zirconium salt solution which is soluble in the conditions of preparation.

Suitable water soluble cerium compounds include Ce III salts, like nitrates or halides such as chlorides, for instance. The soluble zirconium salts used in the invention can be, nitrates, sulfates, or halides, for instance, zirconium sulfate, zirconyl nitrate or zirconyl chloride. Zr (IV) salts can be utilized.

The amount of cerium and zirconium contained in the mixture corresponds to the stoichiometric proportion required to obtain the desired final composition. It is preferable to utilize a cerium or zirconium salt with a high degree of purity, most preferably above about 99%.

Optionally an oxidizing agent can be used. Among the oxidizing agents which are suitable are solutions of sodium, potassium or ammonium perchlorate, chlorate, hypochlorite, or persulfate, hydrogen peroxide or air, oxygen or ozone. An oxidizing agent, preferably hydrogen peroxide, can be added to the cerium/zirconium mixture or to the cerium or zirconium salt before mixing together. The amount of oxidizing agent in relation to the salts to be oxidized can vary within wide limits. It is generally greater than the stoichiometry and preferably corresponds to an excess.

The precipitation can be carried out by the reaction of the salt solution or solutions and a base solution. The base solution can be added to the cerium and or zirconium salt solution to precipitate out the hydroxides or the salt solutions can be added to the base solution. The base can be an ammonia solution or alkaline hydroxide solution, e.g., sodium, potassium, etc. The base solution used can, in particular, be an aqueous solution of ammonia or of sodium or potassium hydroxide. An ammonia solution is preferably used. The normality of the base solution is not a critical factor in accordance with the invention; it can vary within wide limits.

The precipitation is carried out on a batch or continuous basis. In the case of a continuous precipitation, the pH of the reaction is typically maintained between about 7 and about 11, preferably between about 7.5 and about 9.5. The residence time of the material in the reactor is typically at least about 15 minutes, preferably at least 30 minutes. The reaction can be carried out at any suitable temperature such as room temperature. In the case of batch precipitation, the amount of base added is preferably at least the amount required to precipitate out $Ce(OH)_4$ and $Zr(OH)_4$.

After the reaction stage, a solid precipitate is recovered from the reactor and separated from the mother liquor by any known process, for example filtration, settling or centrifugation. The precipitate can be separated by conventional solid/liquid separation techniques such as decanting, drying, filtration and/or centrifuging. The obtained precipitate can optionally then be washed.

The next stage of the process is calcination of the material, either with or without an intermediate drying step. This allows the formation of a crystalline solid solution phase. Usually, the calcination is carried out at temperatures ranging from about 200 to about 1000° C. Calcination temperatures of greater than about 300° C. are suitable, preferably ranging from about 350 to about 800° C.

Usually, Ce/Zr mixed oxides and solid solutions are fine powders, with a particle size lower than about 10 microns. They can be granulated or extruded by any of the known processes to prepare an active support.

The dehydrogenation catalyst compositions of the present invention comprise the cerium/zirconium mixed oxide or solid solution as an active support, an iron catalytic component, and a potassium catalyst promoter. Generally, the catalyst compositions of the present invention comprise, by weight, from about 5% to about 30% of an iron catalytic component; from about 40% to about 60% of a potassium catalyst promoter; and from about 10% to about 60% of the active support.

The improved catalysts of the present invention generally are prepared by admixing the active support component, iron catalytic component and catalyst promoter (potassium compound) and any optional components followed by drying and calcining the resulting mixture, preferably at about 750° C. or greater. Generally, calcination temperatures range from about 500° C. to about 800° C. The catalyst composition of the present invention can be prepared in various ways known to the art.

One method comprises ballmilling together a mixture of the desired compounds, adding a small amount of water, and extruding the composite to produce small pellets, which are then dried and calcined. Another method is mixing the components together with water, drying them to form a powder and tabletizing. Another procedure involves mixing the components together with an excess of water, partially drying, and then subsequently extruding, drying and calcining the resulting pellets.

The dehydrogenation catalyst compositions of the present invention contain iron as an essential catalytic component. An iron salt such as iron citrate is a suitable iron catalytic component. Many forms of iron oxide are used in preparing dehydrogenation catalysts and are suitable as iron catalytic components. While various forms of iron oxide can be employed in the compositions of the present invention, the preferred form employed in the catalytic compositions of the present invention is red iron oxide or a mixture of red iron oxide ($Fe_2O_3$) and yellow iron oxide ($Fe_2O_3.H_2O$).

The dehydrogenation catalyst compositions of the present invention can also contain as a catalyst promoter, one or more potassium compounds. The potassium promoter material can be added to the catalyst in various forms. For example, it may be added as the oxide, or as other compounds which are convertible, at least in part, under calcination conditions, to the oxide. The hydroxides, carbonates, bicarbonates, and the like are suitable. The potassium compound is preferably present in the catalyst as potassium carbonate ($K_2CO_3$) or as a mixture thereof with potassium oxide.

The iron and potassium catalytic promoter form catalitically active Fe/K mixed oxides.

Other known catalyst additives can be included in the catalysts of the invention, but are not essential. Thus, an optional component of the catalyst composition of the invention is a chromium compound which serves as a stabilizer for the active catalytic components. Chromium compounds have, in fact, typically been added to alkali-promoted iron oxide catalysts to extend their life. Chromium, as used in the compositions of this invention, can be added to the catalyst in the form of a chromium oxide or in the form of chromium compounds which decompose upon calcination to chromium oxides, as for example, chromium nitrates, hydroxides, acetates, and the like. If potassium chromates are used, such materials can, of course, also contribute to the requisite concentration of potassium essentially present in the dehydrogenation catalyst compositions as hereinbefore discussed.

A second optional component, used to improve the selectivity of the catalyst, is molybdenum which can be added as its oxide or as a molybdate.

The physical strength, activity and selectivity of the catalyst compositions of the present invention may be improved by adding certain binding agents. Binding agents can include, for example, calcium aluminate or Portland cement. These cements can be added individually or in combination.

The density of the catalyst compositions herein can likewise be modified by the addition of various filler substances, for example, combustible materials such as graphite and methyl cellulose. Such materials can be added to the compositions during preparation but are burned out after the catalyst pellets have been formed during the calcining step. These porosity promoting aids can also facilitate extrusion of catalyst pellets.

The catalysts of the present invention are especially effective in promoting the dehydrogenation of ethylbenzene to produce styrene. Such a dehydrogenation reaction is usually carried out at reaction temperatures of from about 500° C. to about 700° C. However, higher or lower temperatures may be used as are known to those skilled in the art. The use of subatmospheric, atmospheric, or superatmospheric pressures are suitable. However, since it is preferred to operate at as low a pressure as is feasible, atmospheric or subatmospheric pressure is preferred. The process is preferably carried out as a continuous operation. It is preferred to utilize a fixed bed which may consist of a single stage or a series of stages of the same catalyst in one or several reactors. Steam/water can be added to the hydrocarbon reactant feed to aid in the removal of carbonaceous residues from the catalyst. The contact time of the reactant-containing gas with the catalyst is expressed in volume of liquid hydrocarbon reactant per volume of catalyst per hour. The determination of the range of LHSV to effect the degree of conversion desired for the particular feed in question is within an artisan's skill.

Any known method for the production of styrene can be utilized. U.S. Pat. No. 3,733,327, Vrieland et al., issued May 15, 1973; U.S. Pat. No. 4,758,543, Sherrod et al., issued Jul. 19, 1988 and U.S. Pat. No. 5,023,225, Williams et al., issued Jun. 11, 1991 contain descriptions of processes for production of styrene and to that extent are incorporated herein by reference.

The use of the active supports of the present invention or catalysts obtained from these materials after mixing or reaction with a Fe and a K salt and/or after treatment of these materials at high temperature and/or after granulating or extruding these materials for dehydrogenation of ethylbenzene to styrene achieves significant benefits which are illustrated in the following examples.

The following examples are provided to better describe the present invention. They are for illustrative purposes and it is realized that changes and variations may be made with respect to these compositions that are not shown below. Such changes or variations which do not materially alter the compositions, formulation, process or function are still considered to fall within the spirit and scope of the invention as recited by the claims that follow.

EXAMPLES

A catalyst is prepared by mixing ceria ($CeO_2$) with potassium carbonate and iron oxide ($Fe_2O_3$) to obtain the following composition:

$Fe_2O_3$: 2.5%

$K_2O$: 2.5%

$CeO_2$: 95%

Another catalyst is prepared as described previously, but instead of ceria a $(Ce,Zr)O_2$ solid solution containing 80% $CeO_2$ and 20% $ZrO_2$ obtained by co-thermohydrolysis is used. The final composition is:

$Fe_2O_3$: 2.5%

$K_2O$: 2.5%

$CeO_2$: 76%

$ZrO_2$: 19%

After ballmilling grinding, the mixed powders are calcined at about 750° C. for about 2 hours. The dehydrogenation of ethylbenzene is performed in a 240 mm long 316L stainless steel tube, with an inlet for the compounds to be dehydrogenated and the gases and an outlet for reacted compounds. The catalytic test is equipped with 2 chomatographs. The first one has a FID detector (Column filled up with silicocel+10% FFAP) and the second one has a catharometer (column filled up with Hayesep A). The reactor is heated with a fluidized sand bath. The catalyst is diluted in the reactor with glass beads.

Example 1

The reactor is loaded with about 27.2 g of catalyst based on ceria (20 $cm^3$). The temperature is adjusted to about 550° C. and a mixture of about 27.2 ml water and about 15.63 ml ethylbenzene per minute is sprayed to the reactor. The carrier gas is nitrogen with a flow rate of about 3.28 l/h. The pressure is slightly above atmospheric. The conversion and selectivity are measured after a 2 hour test run.

The results are as follows:

Conversion: 60%

Styrene selectivity: 85.1%

Example 2

The experiment of example 1 is repeated with the catalyst based on $(Ce, Zr)O_2$.

The results are as follows:

Conversion: 77.5%

Styrene selectivity: 90.0%

These results demonstrate the improvement due to $(Ce, Zr)O_2$.

What is claimed is:

1. A dehydrogenation catalyst composition comprising:
   an active support selected from the group consisting of cerium/zirconium mixed oxides, cerium/zirconium solid solutions, and mixtures thereof;
   an iron catalytic component; and
   a potassium catalyst promoter.

2. A dehydrogenation catalyst composition according to claim 1, wherein said active support is thermally stable at temperatures higher than 800° C.

3. A dehydrogenation catalyst composition comprising: an active support selected from the group consisting of cerium/zirconium mixed oxides, cerium/zirconium solid solutions and mixtures thereof; an iron catalytic component and potassium catalyst promoter.

4. The dehydrogenation catalyst composition according to claim 3, wherein
   i) from about 5% to about 30%, by weight of the composition, is said iron catalytic component;
   ii) from about 40% to about 60%, by weight of the composition, is said potassium catalyst promoter; and
   iii) from about 10% to about 60%, by weight of the composition, is said active support.

5. The dehydrogenation catalyst composition according to claim 4, further comprising a binding agent.

6. A process for making a dehydrogenation catalyst composition comprising the steps of: a) admixing an active support selected from the group consisting of cerium/zirconium mixed oxides, cerium/zirconium solid solutions and mixtures thereof; an iron catalytic component; and a potassium catalyst promoter; and b) calcining the admixture.

7. A process according to claim 6, further comprising the step of adding water to the admixture prior to calcining.

8. A process according to claim 7, wherein said calcination of the admixture is at about 750° C. for about 2 hours.

9. A process according to claim 6, wherein said active support is produced by a co-precipitation or co-thermohydrolysis process.

10. A dehydrogenation catalyst composition produced by a process comprising the steps of: a) admixing an active support selected from the group consisting of cerium/zirconium mixed oxides, cerium/zirconium solid solutions and mixtures thereof; an iron catalytic component; and a potassium catalyst promoter; and b) calcining the admixture to form a catlyst composition.

11. A dehydrogenation catalyst composition produced by a process comprising the steps of:
   (a) preparing an admixture comprising an active support selected from the group consisting of i) cerium/zirconium mixed oxides, cerium/zirconium solid solutions, and mixtures thereof, ii) an iron catalytic component, and iii) a potassium catalyst promoter;
   (b) adding water to said admixture; and
   (c) calcining said water-containing admixture.

12. A dehydrogenation catalyst composition produced by a process comprising the steps of:
   (a) preparing an admixture comprising an active support selected from the group consisting of i) cerium/zirconium mixed oxides, cerium/zirconium solid solutions, and mixtures thereof, ii) an iron catalytic component, and iii) a potassium catalyst promoter;
   (b) adding water to said admixture; and
   (c) calcining said water-containing admixture at about 750° C. for about 2 hours.

* * * * *